(12) United States Patent
Johnson et al.

(10) Patent No.: US 12,078,702 B2
(45) Date of Patent: Sep. 3, 2024

(54) IMAGE SIGNAL REPRESENTING A SCENE

(71) Applicant: KONINKLIJKE PHILIPS N.V., Eindhoven (NL)

(72) Inventors: Brian David Johnson, Dallas, TX (US); Ivan Dimitrov, Coppell, TX (US); Sandeep K. Ganji, Dallas, TX (US)

(73) Assignee: Koninklijke Philips N.V., Eindhoven (NL)

( * ) Notice: Subject to any disclaimer, the term of this patent is extended or adjusted under 35 U.S.C. 154(b) by 415 days.

(21) Appl. No.: 17/428,298

(22) PCT Filed: Feb. 5, 2020

(86) PCT No.: PCT/EP2020/052902
§ 371 (c)(1),
(2) Date: Aug. 4, 2021

(87) PCT Pub. No.: WO2020/161204
PCT Pub. Date: Aug. 13, 2020

(65) Prior Publication Data
US 2022/0155395 A1    May 19, 2022

Related U.S. Application Data

(60) Provisional application No. 62/801,726, filed on Feb. 6, 2019.

(51) Int. Cl.
*G01R 33/48* (2006.01)
*G01R 33/483* (2006.01)
(Continued)

(52) U.S. Cl.
CPC ..... *G01R 33/4818* (2013.01); *G01R 33/4835* (2013.01); *G01R 33/5608* (2013.01);
(Continued)

(58) Field of Classification Search
CPC ........... G01R 33/4818; G01R 33/4835; G01R 33/5608; G01R 33/5619; G01R 33/56545; A61B 5/004; A61B 5/055
(Continued)

(56) References Cited

U.S. PATENT DOCUMENTS 7,358,727 B1    4/2008  Angelos
2003/0060698 A1  3/2003  Mistretta
(Continued)

OTHER PUBLICATIONS

International Search Report and Written Opinion from PCT/EP2020/052902 mailed Aug. 13, 2020.
(Continued)

*Primary Examiner* — Gabriel I Garcia

(57) ABSTRACT

To reduce instances of patient call back examinations and longer acquisition times in MRI, caused by features noticed at the periphery of a prescribed field of view (FOV) image, an extended field of view (EFOV) image is generated by storing k-space data including oversampling data, in a Picture Archiving and Communication System (PACS) and/or technician workstation. The saved k-space data is repurposed to re-reconstruct the (EFOV) image before any cropping operation on the prescribed FOV. In another application, the extended (EFOV) image is generated by repurposing stored k-space oversampling data, from adjacent or overlapping fields of view (FOV). The disclosed device and method can be used advantageously in a multi-station MRI IT system and/or spinal MRI examinations.

21 Claims, 5 Drawing Sheets

(51) Int. Cl.
  *G01R 33/56* (2006.01)
  *A61B 5/00* (2006.01)
  *A61B 5/055* (2006.01)
  *G01R 33/561* (2006.01)
  *G01R 33/565* (2006.01)

(52) U.S. Cl.
  CPC ............... *A61B 5/004* (2013.01); *A61B 5/055* (2013.01); *G01R 33/5619* (2013.01); *G01R 33/56545* (2013.01)

(58) Field of Classification Search
  USPC ........................................................ 382/128
  See application file for complete search history.

(56) References Cited

U.S. PATENT DOCUMENTS

| | | |
|---|---|---|
| 2007/0007960 A1 | 1/2007 | King et al. |
| 2008/0240533 A1 | 10/2008 | Piron et al. |
| 2012/0296199 A1 | 11/2012 | Kim et al. |
| 2013/0113486 A1 | 5/2013 | Imamura et al. |
| 2013/0137968 A1 | 5/2013 | Reisman et al. |
| 2013/0195342 A1* | 8/2013 | Haacke ................ G01R 33/443 382/131 |
| 2014/0212012 A1 | 7/2014 | Fain et al. |
| 2015/0054505 A1 | 2/2015 | Wang et al. |
| 2016/0245889 A1 | 8/2016 | Djeridane et al. |
| 2017/0261584 A1* | 9/2017 | James ................ G01R 33/4833 |
| 2017/0319154 A1 | 11/2017 | Andreyev et al. |
| 2018/0088200 A1 | 3/2018 | Schmitt |
| 2018/0188342 A1 | 7/2018 | Heberlein et al. |
| 2018/0365876 A1 | 12/2018 | Wimmer et al. |

OTHER PUBLICATIONS

O'Connor et al "A Review of Cross-Sectional Imaging, Ultrasound and Nuclear Medicine Utilization Patterns in Irelands" Paediatric Patients Br. J Radil. Apr. 2015;88(1048):20140767.

* cited by examiner

IMAGE SIGNAL REPRESENTING A SCENE

CROSS REFERENCE TO RELATED APPLICATIONS

This application is a U.S. national phase application of International Application No. PCT/EP2020/052902 filed on Feb. 5, 2020, which claims the benefit of U.S. Provisional Application Ser. No. 62/801,726 filed on Feb. 6, 2019 and is incorporated herein by reference.

FIELD

The following relates generally to the magnetic resonance imaging (MRI) arts, MRI image reconstruction arts, spinal MRI examination arts, multi-station MRI examination arts, and related arts.

BACKGROUND

In MRI, to avoid aliasing or wrap in an image of a prescribed field of view (FOV), it is known to oversample in the readout, phase encode, and slice directions. For readout, the oversampling can be performed without cost in increased acquisition time. However, phase encode oversampling increases the acquisition time, as does slice oversampling which entails acquiring additional slices extending beyond the boundary of the prescribed FOV. The acquired k-space data including the oversampling data are reconstructed to generate an image that is larger in spatial extent than the prescribed FOV due to the oversampling. This image is then cropped to retain only the prescribed FOV, without aliasing or wrap. The image is uploaded to the Picture Archiving and Communication System (PACS) and forms the final clinical image that is retrieved from the PACS and reviewed by a clinician.

The following discloses certain improvements.

SUMMARY

In some non-limiting illustrative embodiments disclosed herein, a method for reconstructing an image of a subject in a MRI IT system comprising: acquiring k-space data including oversampling k-space data for a prescribed field of view (FOV) image of the subject; and storing the acquired data and the specific angulation data used for the acquisition in a non-transitory storage medium; processing the stored data to reconstruct a first extended field view (EFOV) image; cropping the first EFOV image to generate the prescribed FOV image without aliasing or wrap artifacts; displaying the prescribed (FOV) image; and reusing the stored data to re-reconstruct a second extended (EFOV) image; and displaying the second extended field of view (EFOV) image.

In some non-limiting illustrative embodiments disclosed herein, a device for reconstructing an image of a subject in a MRI IT system by repurposing image data comprising a non-transitory storage medium for storing acquired k-space data including oversampling k-space data for a plurality of prescribed field of view (FOV) images that are adjacent or overlapping of the subject and have the same angulation; a processor for processing the stored data to reconstruct at least one of the prescribed field of view (FOV) images and an extended field of view (EFOV) image of the prescribed FOV image without any aliasing or wrap artifacts by repurposing k-space oversampling data from the adjacent or overlapping prescribed (FOV) images; and a display for displaying the prescribed (FOV) image and the extended field of view (EFOV) image.

In some non-limiting illustrative embodiments disclosed herein, a method of repurposing image data in a MRI IT examination of a subject comprising: acquiring k-space data including oversampling k-space data for a number of prescribed field of view (FOV) images of the subject that are adjacent or overlapping and have the same angulation; storing the acquired data in a non-transitory storage medium; processing the stored data to reconstruct at least one of the prescribed field of view (FOV) images and an extended field of view (EFOV) image of the prescribed FOV image without any aliasing or wrap artifacts by repurposing k-space oversampling data from adjacent or overlapping prescribed (FOV) images; and displaying the prescribed (FOV) image and the extended field of view (EFOV) image.

One advantage resides in reduced magnetic resonance imaging (MRI) examination data acquisition times and improved patient workflow efficiency.

Another advantage resides in reduced instances of patient call back examinations.

Another advantage resides in improved diagnostic performance of MRI examinations by providing additional field of view when clinically advantageous without concomitant increase in MRI examination data acquisition time.

Another advantage resides in providing an MRI information technology (IT) infrastructure facilitating one or more of the above-mentioned benefits and/or other benefits.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The invention may take form in various components and arrangements of components, and in various steps and arrangements of steps. The drawings are only for purposes of illustrating the preferred embodiments and are not to be construed as limiting the invention.

DETAILED DESCRIPTION

Figure 1:
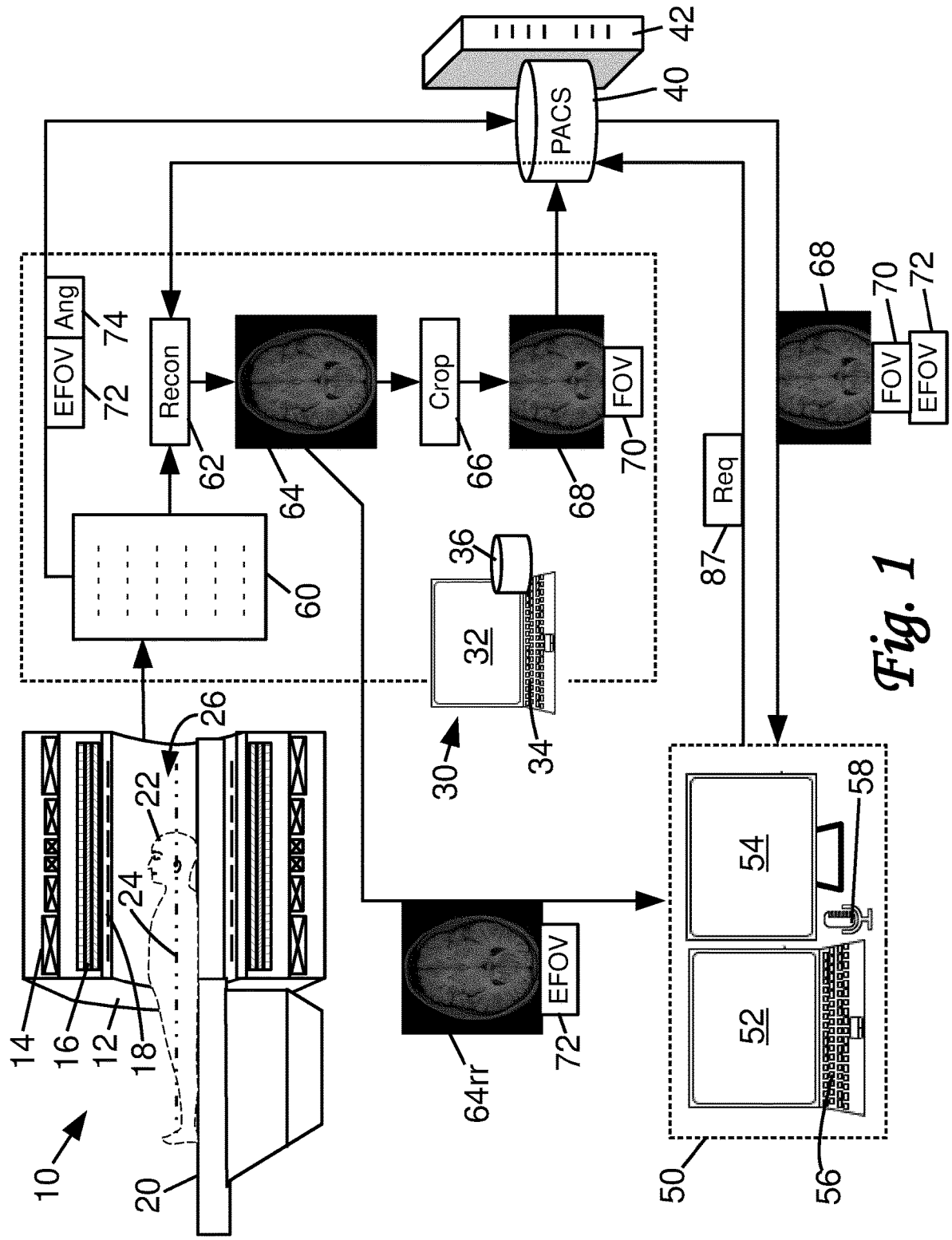
FIG. 1 diagrammatically illustrates a magnetic resonance imaging (MRI) information technology (IT) infrastructure including aspects facilitating re-use of acquired k-space data as oversampling data and/or to increase image field of view (FOV).

As noted previously, in a conventional magnetic resonance imaging (MRI) information technology (IT) infrastructure, the acquired k-space data including the oversampling data are reconstructed to generate an image in an extended field of view (FOV) that encompasses and is larger than the prescribed FOV due to the oversampling. This image is then cropped to the prescribed FOV (in the cropping operation, portions of the image outside of the prescribed FOV are removed leaving only the portion of the image in the prescribed FOV), without aliasing or wrap, which is uploaded to the PACS and forms the final clinical image that is reviewed by a clinician. In a conventional MRI IT infrastructure, the acquired k-space data (with or without the oversampling data) is typically not stored on the PACS, and is typically also not stored at the MRI technician's workstation.

It is recognized herein that there are certain situations in which the acquired k-space data, and especially the oversampling data, may be advantageously stored and later reused or repurposed. In one such situation, the clinician may notice a feature (or a portion of a feature) at the periphery of the image of the prescribed FOV. As the oversampling data are conventionally not stored in the PACS or at the MRI technician's workstation, the clinician must either attempt to determine a clinical finding from the existing image of the prescribed FOV, or may decide to order a call back MRI examination with a larger or shifted prescribed FOV in order to better capture the noticed feature or feature portion. It is recognized herein that these unsatisfactory options can be avoided by storing the acquired k-space data including the oversampling data in the PACS and/or at the MRI technician's workstation, and repeating the reconstruction of the extended FOV without the subsequent cropping to the originally prescribed FOV. The resulting image will have the extended FOV, and may be transmitted to the clinician for use in the clinical reading of the MRI images. Although portion of the image in the additional FOV (that is, outside of the originally prescribed FOV) may have some aliasing or wrap due to the lack of oversampling for the extended FOV, it nonetheless provides useful image content for assessing the noticed feature or feature portion, without the cost and inconvenience to the patient that would be introduced by ordering a call back MRI examination. Even with some possible aliasing or wrap, the additional image content can provide useful context.

In another situation, a clinician may order two or more MRI examinations of different, but adjacent or overlapping, anatomical regions. For example, one such situation which commonly arises is in MRI spinal examination. Spine MRI examinations are the most commonly ordered MRI examination, and by some estimates accounts for about one-quarter of all MRI examinations. Often, examinations of more than one section of the spine are ordered, e.g. a cervical spine MRI examination, a thoracic spine MRI examination, and/or a lumbar spine MRI examination. This is especially the case when it comes to certain pathologies like bone metastases, multiple sclerosis, cord compression, and so forth. These spinal MRI examinations commonly employ administration of contrast agent, and therefore post-contrast imaging is performed which extends the time the patient is on the table. Total spine examinations require patients to lie still and be scanned for long periods of time which leads to a higher percentage of patients moving, thus leading to decreased image quality and potentially undiagnostic scans. These exams also lead to large amounts amount of radio frequency (RF) exposure by the patient resulting in a high specific energy dose (SED). Additionally, total spine imaging occupies the MRI scanner for a lengthy time interval, thus reducing the productivity of the MRI scanner and also making it difficult to schedule the long time block for the spinal MRI examination.

In embodiments disclosed herein, when spinal MRI examinations of two adjacent or overlapping anatomical regions are performed (e.g. a cervical MRI and a thoracic MRI; or, a thoracic MRI and a lumbar MRI), then the k-space data acquired for one MRI examination (e.g. the thoracic MRI) may be re-used to provide oversampling k-space data from the other MRI examination (e.g. the cervical MRI in this example). In the case of a complete spinal examination including cervical, thoracic, and lumbar MRI examinations, such re-use of k-space data can reduce the scan time for the total spine by approximately two-thirds, thereby enhancing patient comfort and improving compliance, safety, and increasing workflow efficiency for the MRI scanner. Such re-use of k-space data is facilitated because the spine is a piece of anatomy with a long, relatively straight, and continuous structure. The cervical spine sits superior and adjacent to the thoracic spine, while the lumbar sits inferior and adjacent to the thoracic spine. Because the cervical, thoracic, and lumbar spine sections are similar in structure and adjacent to each other re-use of k-space data from MRI examinations of adjacent anatomical regions to provide oversampling k-space data to correct for aliasing/wrap serves to accelerate the MRI examination.

Re-use of MRI k-space data to provide oversampling k-space data is more generally feasible in any situation in which two MRI examinations of adjacent or overlapping fields of view are performed, and in which the k-space data for both MRI examinations are performed with the same angulation (that is, the same angular orientations of the slice select, phase encode, and readout directions). Consonance of other acquisition parameters such as the slice thickness and resolution is also helpful, although conversions can adjust for differences in some acquisition parameters (e.g. resampling can compensate for differences in slice thickness and/or resolution).

With reference to FIG. 1, an illustrative MRI IT infrastructure is shown, which facilitates approaches for k-space data re-use disclosed herein. A magnetic resonance imaging (MRI) scanner 10 includes typical components such as a housing 12 containing a main magnet 14 (typically comprising superconducting windings, although a resistive magnet is also contemplated), a set of magnetic field gradient coils 16, an optional whole-body radio frequency (RF) coil 18 (additionally or alternatively, various local RF coils, RF coil arrays, and/or so forth may be employed for RF excitation and/or magnetic resonance readout), a patient support 20 (preferably although not necessarily including robotic actuators for patient positioning) for moving a patient 22 along an axial direction 24 into and out of an examination region (in the illustrative case, the examination region is within a bore 26 of the housing 12, although other MRI configurations such as a vertical-magnet MRI, open-bore MRI, or so forth are also contemplated), and so forth. While a single MRI scanner 10 is illustrated, it will be appreciated that some MRI laboratories may include one, two, three, or more MRI scanners of various types.

The illustrative MRI IT infrastructure further includes an MRI controller 30 that provides user interfacing of an MRI technician with the MRI scanner 10 in order to program and/or control the MRI scanner 10 to perform a desired MRI examination, such as a brain MRI examination, a spinal MRI examination, and/or so forth. The MRI controller 30 includes an electronic processor (not shown, e.g. a microprocessor, possibly multi-core or otherwise configured as is known in the digital electronics arts), a display 32, and one or more user input devices such as an illustrative keyboard 34 (and/or a mouse, trackpad, touch-sensitive overlay of the display 32, and/or so forth). The MRI controller 30 typically also includes a local non-transitory data storage medium 36, such as a hard disk drive, solid state drive (SSD), flash memory, and/or so forth, for local storage of k-space data acquired by the MRI scanner 10 and/or for other purposes. The illustrative MRI controller 30 is embodied as a computer with appropriate peripherals 32, 34, 36. While a single MRI controller 30 is illustrated, it will be appreciated that in some embodiments in which the MRI laboratory includes multiple MRI scanners there may be multiple MRI controllers for the MRI scanners.

The illustrative MRI IT infrastructure further includes a Picture Archiving and Communication System (PACS) comprising a non-transitory data storage medium 40 (e.g. a hard disk drive, solid state drive or SSD, redundant array of independent disks or RAID, various combinations thereof, and/or so forth) and associated electronic processor(s), e.g. embodied in the illustrative example by a network-based server computer 42. The PACS 40, 42 stores MRI images and possibly images of other medical imaging modalities (e.g., PET, CT, and/or so forth), and the PACS may optionally be integrated with one or more other medical information systems such as a Radiology Information System (i.e. a PACS/RIS system). The PACS 40, 42 provides a network-based storage system for storing medical images, including MRI images, along with relevant metadata (e.g. indicating imaging parameters used in acquiring the images, metadata identifying patient, exam date, reason for exam, anatomical region, imaging modality, and/or so forth). Hence, the MRI controller 30 is connected with the PACS 40, 42 by an electronic data network (e.g. a wired or wireless local area network or LAN, the Internet, various combinations thereof, and/or so forth) to upload images of an MRI examination along with relevant metadata to the PACS 40, 42 for later review by a radiologist, physician, and/or other clinician(s).

The illustrative MRI IT infrastructure further includes a radiology workstation 50 at which a radiologist may review images of an MRI examination and dictate (or type or otherwise input) a radiology report summarizing the radiologist's findings. The radiology workstation 50 is connected with the PACS 40, 42 via the electronic data network to retrieve images and metadata of an MRI examination from the PACS 40, 42 for review by the radiologist. The illustrative radiology workstation 50 includes two displays 52, 54 which can be useful, for example, to allow the radiologist to have images displayed on one display and the radiology report-under-draft displayed on the other display; however, a single display is contemplated, as is having three or even more displays. The radiology workstation 50 further includes one or more user input devices, such as an illustrative keyboard 56, a dictation microphone 58 via which a radiologist can dictate a radiology report, and/or so forth. The radiology workstation 50 typically also includes an electronic processor, and may be embodied in whole or part as a computer with appropriate peripherals (e.g. display 52, 54, user input devices 56, 58). While a single radiology workstation 50 is illustrated, more generally one, two, three, or more radiology workstations may be provided, e.g. to service a staff of radiologists, and/or the MRI IT infrastructure may include other similar clinician workstations (not shown) such as physician office computer(s).

With continuing reference to FIG. 1, an illustrative brain MRI examination is diagrammatically depicted. The MRI controller 30 controls the MRI scanner 10 to acquire k-space data 60 for a field of view (FOV) prescribed by the clinician for the brain MRI examination. The acquired k-space data 60 includes oversampling k-space data sufficient to allow for the prescription FOV to be reconstructed without aliasing or wrap. The k-space data 60 including the oversampling k-space data are reconstructed in an image reconstruction operation 62 (for example, using a Fourier transform image reconstruction, iterative reconstruction, or another image reconstruction algorithm suitable for the spatial encoding employed in the data acquisition). The output of the image reconstruction operation 62 is an image 64 of an extended field of view (EFOV) that encompasses and is larger than the prescription FOV. However, the portions of the image 64 lying outside of the prescription FOV may have some aliasing or wrap. In a crop operation 66, the image 64 of the EFOV is cropped to the prescription FOV to generate an image 68 of the prescription FOV. The cropping of the image removes the portions that may have aliasing or wrap, leaving the image 68 without aliasing or wrap.

The MRI artifact known as aliasing or wrap occurs when there is tissue or anatomy outside of the FOV. Aliasing from tissue outside of the FOV can be eliminated if the MRI signal is adequately sampled, by using oversampling. Aliasing occurs in the phase and frequency directions for two-dimensional imaging. Frequency oversampling can be applied to eliminate aliasing along the frequency encoding direction without any time penalty. However, when tissue lies outside of the FOV in the phase encoding direction, then k-space oversampling in the phase encoding direction is performed at the cost of longer scan times. The phase and frequency oversampling data are then removed by the cropping so the resultant image contains only the prescribed FOV, without any aliasing or wrap in the phase encode direction. Similarly, oversampling and cropping can be performed in the slice select direction if there is anatomy outside the prescription FOV, so as to provide the image with the prescribed FOV without any aliasing or wrap in the slice select direction.

Conventionally, the image 68 of the prescription FOV is the final image that is stored in the PACS 42, 44 along with relevant metadata such as a label of the FOV 70 and acquisition parameters such as slice thickness, resolution, et cetera. The image 68 may then be later retrieved to the radiology workstation 50 for review by the radiologist. A problem can arise, however, if the radiologist decides that the prescription FOV of the image 68 is not sufficient. For example, the radiologist may determine that the desired anatomical region was not within the prescription FOV, or the radiologist may observe a suspicious feature (e.g., possible brain lesion) that is at the periphery of the prescription FOV in the image 68. Conventionally, in such a case the radiologist would need to either determine the clinical findings based on the image 68 in spite of its possibly insufficient field of view, or would have to order a call back brain MRI examination with an updated prescription FOV to obtain an image with the updated FOV.

As disclosed herein, this problem is addressed by retaining and re-using the oversampling k-space data. As diagrammatically shown in FIG. 1, the k-space data 60 is also stored in the PACS 40, 42, preferably tagged with relevant metadata such as a label of the extended field of view (EFOV) 72 and a label of the angulation 74 of the k-space data 60. (It should be noted that the various metadata 70, 72, 74 may be stored in any suitable format, and in particular may be stored in a non-explicit format, e.g. the EFOV 72 may not be stored as explicit spatial dimensions but rather may be stored as data acquisition parameters of the MRI examination from which the EFOV 72 may be derived by known computations).

Figure 2:
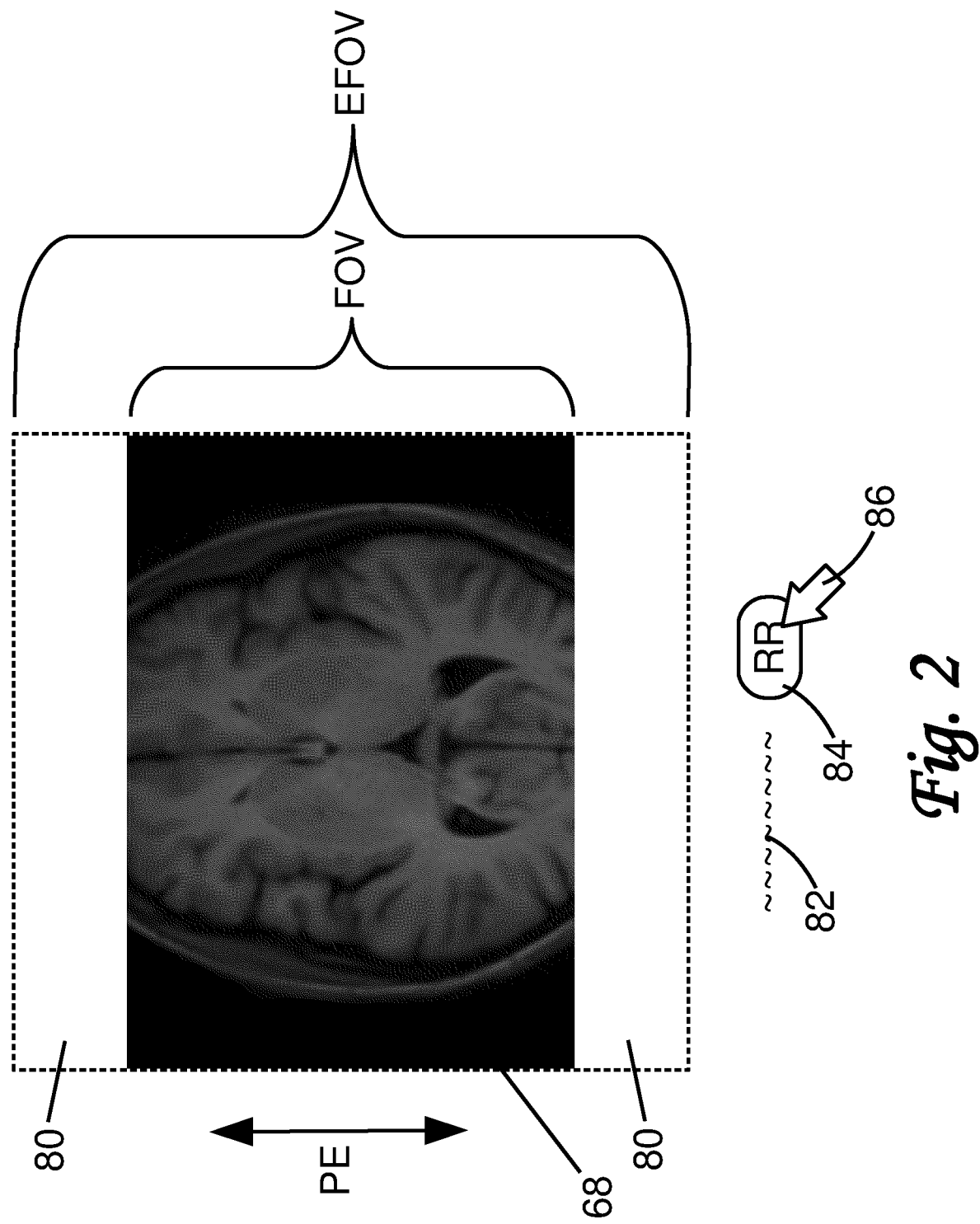
FIG. 2 diagrammatically illustrates display shown on a workstation display or the like of a brain image of a prescribed FOV together with an indication of an extended field of view that is available through re-use of oversampling k-space data in a phase-encoding direction.

With continuing reference to FIG. 1 and with further reference to FIG. 2, when the image 68 of the prescription FOV is retrieved at the radiology workstation 50 it is preferably tagged with the EFOV 72 metadata. FIG. 2 shows a display of the image 68 on the display 52 (or on the display 54) of the radiology workstation 50. In addition to displaying the image 68, the display also includes an indication 80 of the EFOV 72. In the illustrative example of FIG. 2, the image 68 is an axial slice of the brain, and the phase encode (PE) direction is along the anterior-posterior anatomical direction. Hence, the EFOV 72 includes additional image content extending beyond the prescription FOV along the PE direction, and the spatial area of this additional image content is indicated in the illustrative example by a dashed rectangular outline 80 of the available extension in the illustrative display presentation of FIG. 2. Other graphical representations of the indication 80 of the EFOV 72 are contemplated, such as using hatching or crosshatching, shading, color, or so forth to denote the additional image content that is available. The illustrative display further includes a diagrammatically indicated textual message 82 (represented by tilde symbols, i.e. "~~~~~~~" in FIG. 2) asking whether to increase the field of view to that indicated by the indication 80. Preferably, although not necessarily, the textual message 82 informs the user that the additional image content that can be generated for the area indicated by indication 82 may have aliasing or wrap. If the user selects to increase the FOV, e.g. in the illustrative example by selecting a "RR" (re-reconstruct") selection button 84 using a mouse pointer 86, although other user inputs for requesting to increase the field of view are contemplated, then the oversampling k-space data in the phase encoding direction is re-used for this purpose. As shown in FIG. 1, the re-reconstruction request 87 generated by the selection of the button 84 triggers retrieval of the k-space data 60 including the oversampling k-space data from the PACS 40, 42 and re-reconstruction of this data 60 is performed by the reconstruction operation 62. However, instead of then transferring the re-reconstructed image 64 to the crop operation 66, it is instead sent as a re-reconstructed image 64rr of the EFOV 72 to the radiology workstation 50 for display on the display 52, 54. In this way, the radiologist is provided with the additional image content in the regions of the indication 80 (albeit possibly with some aliasing or wrap).

Figure 3:
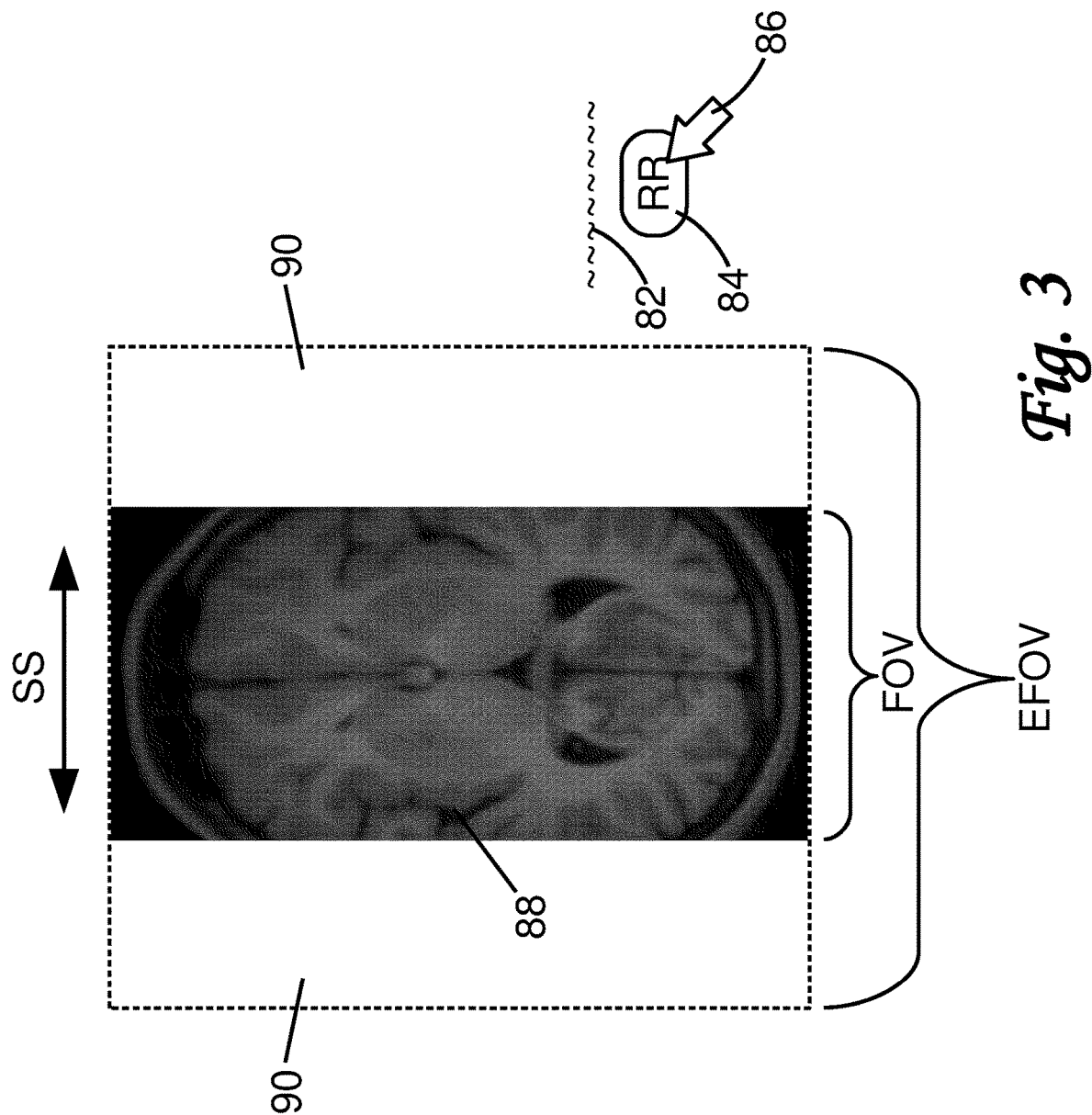
FIG. 3 diagrammatically illustrates display shown on a workstation display or the like of a brain image of a prescribed FOV together with an indication of an extended field of view that is available through re-use of oversampling k-space data in a slice select direction.

With brief reference to FIG. 3, it will be appreciated that analogous processing can be performed to provide the user with the option to extend the image into an extended field of view (EFOV) along a slice select (SS) direction which in the illustrative example of FIG. 3 of an axial brain slice is along the anatomical lateral-medial direction. Again, the textual message 82 is presented asking whether to increase the field of view to that indicated by an indication 90. If the user selects to increase the FOV, e.g. in the illustrative example by selecting the "RR" (re-reconstruct") selection button 84 using the mouse pointer 86, then the oversampling k-space data in the slice select direction is re-used for this purpose. (In this case, the oversampling k-space data are additional peripheral slices of k-space data acquired to fill in the areas indicated by the indications 90). The k-space data including the oversampling k-space data in the slice-select direction is retrieved from the PACS 40, 42 and re-reconstruction of this data is performed by the reconstruction operation 62. However, instead of then cropping to the prescription FOV, the uncropped image with the EFOV is instead sent as a re-reconstructed image of the EFOV to the radiology workstation 50 for display on the display 52, 54. In this way, the radiologist is provided with the additional image content in the regions of the indication 90 (again, possibly with some aliasing or wrap).

In the illustrative examples of FIG. 1, all image reconstruction or re-reconstruction is via the reconstruction operation 62 performed by the MRI controller 30. However, other distributions of the computational load are contemplated. For example, the PACS 42, 44 may include programming to perform the re-reconstruction operation, or the radiology workstation 50 may be programmed to perform the re-reconstruction operation. Moreover, while the image display operations and the request to extend the field of view are executed by the radiology workstation 50 in the illustrative example, such may be done at another workstation such as a clinician's workstation.

Although not illustrated, when the re-reconstructed image 64rr having the EFOV is displayed at the radiology workstation 50 (or other clinician's workstation), it is contemplated to include the indications 80 to indicate to the radiologist or other clinician which areas of the image of the EFOV may have some aliasing or wrap.

Figure 4:
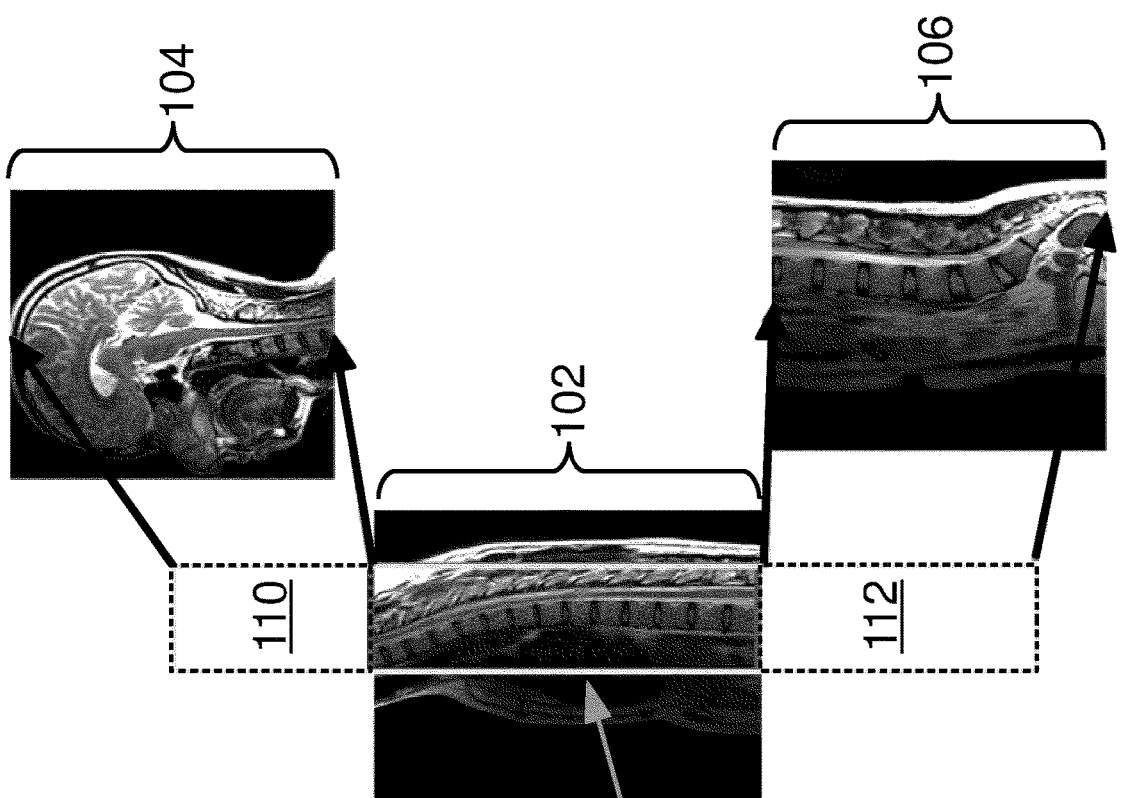
FIG. 4 diagrammatically illustrates re-use of data from a cervical spine MRI examination, a thoracic spine MRI examination, and a lumbar spine MRI examination to provide oversampling k-space data in the respective MRI examinations.
Figure 4:
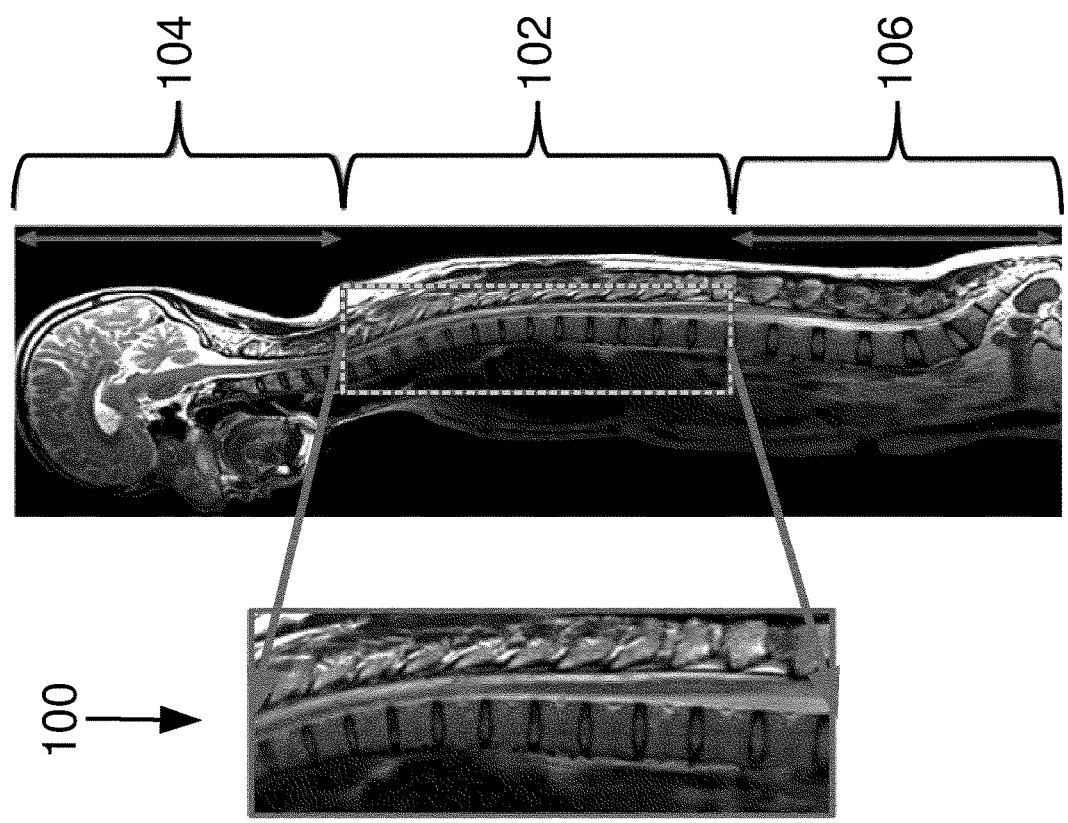

With reference now to FIG. 4, in another application, k-space data acquired for one MRI examination is reused to provide oversampling k-space data for another MRI examination of an adjacent or overlapping field of view. The example of FIG. 4 applies this to spinal MRI examinations. The left-most image 100 of FIG. 4 depicts an image of a thoracic spinal MRI study 102. To reconstruct the image 100 without aliasing or wrap, it is necessary to reconstruct k-space data for the (prescription) FOV of the image 100 together with oversampling k-space data from the region extending in the superior anatomical direction "above" the FOV of the image 100, and also together with oversampling k-space data from the region extending in the inferior anatomical direction "below" the FOV of the image 100. Conventionally, the acquisition of this oversampling k-space data in the superior and inferior extension areas would be done as part of the thoracic spinal MRI study 102.

However, it is recognized herein that in many MRI spinal examination scenarios, such as spinal MRI examinations ordered in conjunction with pathologies such as bone metastases, multiple sclerosis, cord compression, and so forth, it is common to order the thoracic spinal MRI examination 102 in conjunction with a cervical spinal MRI examination 104, and/or in conjunction with a lumbar spinal MRI examination 106. As diagrammatically shown in the right side of FIG. 4, at least a portion of the k-space data of the cervical spinal MRI examination 104 (if performed along with the thoracic spinal MRI examination 102) may be reused to supply oversampling k-space data in the superior anatomical region 110 located "above" the thoracic FOV of the image 100. Likewise, at least a portion of the k-space data of the lumbar spinal MRI examination 106 (if performed along with the thoracic spinal MRI examination 102) may be reused to supply oversampling k-space data in the inferior anatomical region 112 located "below" the thoracic FOV of the image 100. In order to reuse the data in this way, the three spinal MRI examinations 102, 104, 106 should have the same angulation. Preferably, they should also have other common acquisition parameters, e.g. slice thickness, resolution, and so forth, although this can be compensated by performing resampling of the reused oversampling k-space data.

Although not indicated in FIG. 4, in a similar way the reconstruction of the k-space data of the cervical spinal MRI examination 104 may suitably leverage at least a portion of the k-space data of the thoracic spinal MRI examination 102 to supply oversampling k-space data in the inferior anatomical region relative to the cervical FOV, that is, in the region located "below" the cervical FOV. Likewise, the reconstruction of the k-space data of the lumbar spinal MRI examination 106 may suitably leverage at least a portion of the k-space data of the thoracic spinal MRI examination 102 to supply oversampling k-space data in the superior anatomical region relative to the lumbar FOV, that is, in the region located "above" the lumbar FOV. In the lumbar example, the k-space data of the thoracic spinal MRI 102 provides only one-half of the needed oversampling k-space data as the thoracic spinal MRI 102 cannot provide oversampling k-space data in the inferior anatomical region relative to the lumbar FOV, that is, in the region located "below" the lumbar FOV. Nonetheless, k-space data acquisition for the series of cervical/thoracic/lumbar spinal MRI examinations is significantly reduced by way of the foregoing reuse of k-space data. For example, if the average length of a set of cervical, thoracic, and/or lumbar spinal MRI examinations is 100 minutes, it is estimated that the disclosed approach of reusing k-space data from adjacent spinal MRI examinations as oversampling k-space data as discussed above would save an average of 40 minutes per patient, reducing the average patient scan time to 60 minutes.

While spinal MRI examinations are used as an illustrative example in FIG. 4, it will be appreciated that the disclosed approach is more generally applicable for MRI examinations of any two (or more) adjacent body parts, e.g. along the spine (as per FIG. 4), along long bones, and along the abdomen/pelvis as further examples.

As another application, the approach can be applied for adjacent stations of a multi-station imaging examination, in which successive stations are adjacent or overlapping along the axial direction 24 (as indicated in FIG. 1). In this case, the FOV is a station field of view of the multi-station MRI examination, and the k-space data includes k-space data of the station FOV and k-space data of an adjacent or overlapping station field of view of the of a multi-station MRI examination that is adjacent to or overlaps the station FOV. The reconstruction operation 62 comprises reconstructing the k-space data including as oversampling k-space data the k-space data of the adjacent or overlapping station field of view. The reconstruction 62 generates an extended image of an extended field of view (EFOV) that encompasses the station FOV and extends into the adjacent or overlapping station field of view. The crop operation 66 operates to crop the extended image to the station FOV to generate an image of the station FOV without aliasing or wrap. By this mechanism, the acquired k-space data for each station FOV is reduced, thereby reducing the total scan time for performing the multi-station MRI examination of the patient.

Figure 5:
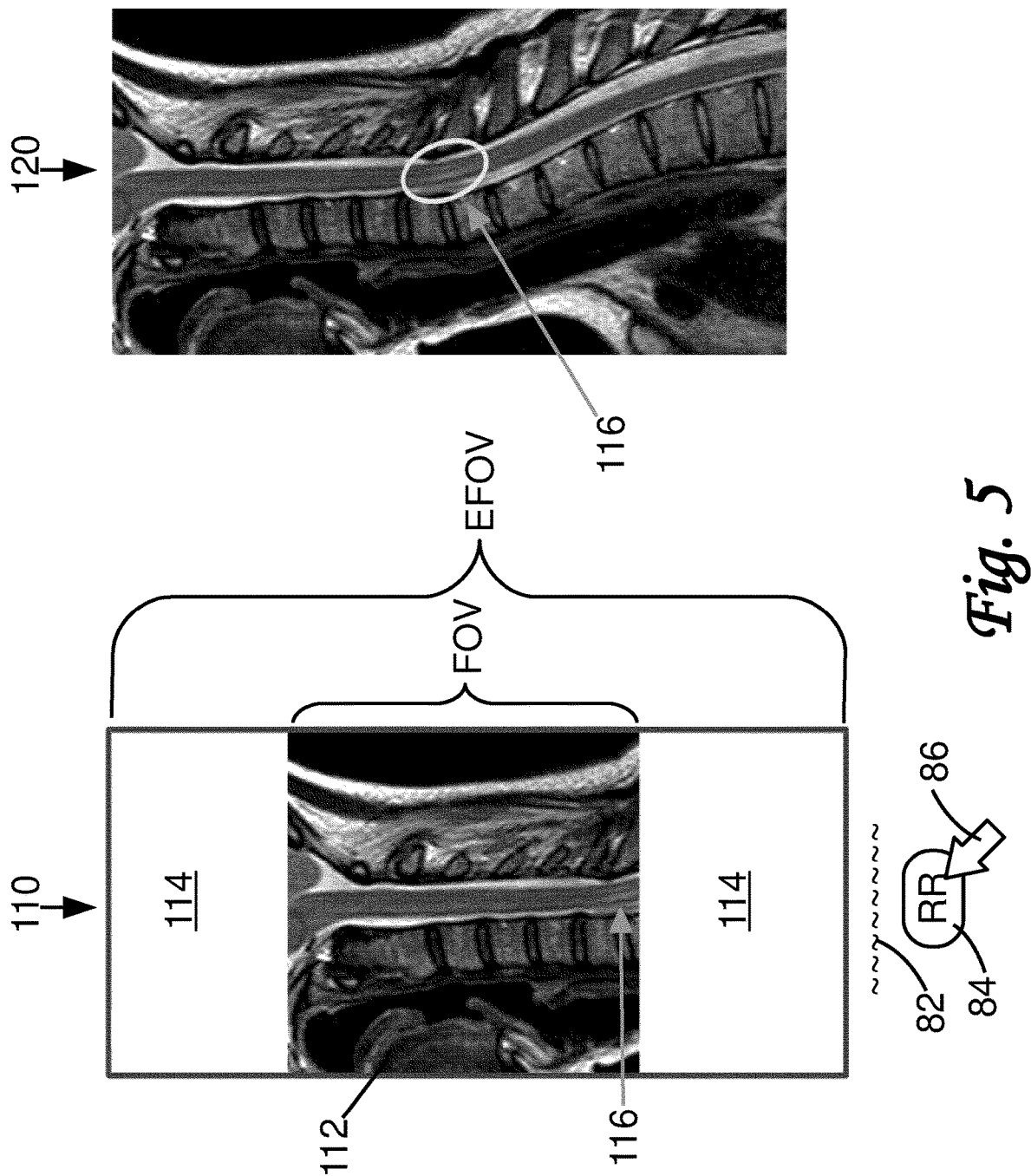
FIG. 5 diagrammatically illustrates re-use of oversampling k-space data to extend a FOV of an image to provide additional/improved imaging of a clinically relevant feature.

With reference to FIG. 5, application of the disclosed approach of re-using oversampling k-space data to provide an enlarged field of view (as described with reference to FIGS. 1-3) is described. In this application, a potential patient call-back MRI examination is avoided. Patient call-backs due to error in properly prescribing the FOV or otherwise missing anatomy or pathology of clinical interest can lead to delays in patient diagnosis, inconvenience to patients, reduced workflow efficiency, and loss in potential revenue. By saving the oversampling k-space data in the PACS 40, 42 as disclosed herein, when this occurs and the relevant anatomy or suspected anatomy is close to, clipped, or just outside the FOV (but within the EFOV) then the images can be re-reconstructed so as to eliminate the need for a call back. In the example of FIG. 5, at the clinician workstation (e.g. the radiology workstation 50) the clinician is presented with a display 110 (left-hand side of FIG. 5) of an image 112 having a prescribed field of view (FOV). The display further includes indications 114 of the additional image content that could be provided by leveraging the oversampling k-space data stored in the PACS 42, 44, along with the user interface dialog text and control 82, 84 described previously with reference to FIGS. 2 and 3. The clinician notices a feature 116 which is at the lower periphery of the FOV of the image 112. Conventionally, the clinician would likely need to order a call-back MRI examination, with a larger or shifted field of view, in order to capture the features 116. However, using the disclosed approach, the clinician selects the button 84 using a mouse controlling the mouse pointer 86 (or, alternatively, some other user interface device) in order to request the re-reconstruction of the extended field of view (EFOV). The re-reconstruction (without subsequent clipping) generates an image 120 of the EFOV, within which the features 116 is well away from the periphery of the image. This approach for reducing call-back MRI examinations is more generally applicable for imaging any body part as long as the clipped or peripheral or missed anatomy or pathology falls within the area covered by the phase/frequency oversampling.

The invention has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A method of reconstructing an image of a subject in a MRI IT system comprising: acquiring k-space data including oversampling k-space data for a prescribed field of view (FOV) image of the subject; and storing the acquired data and the specific angulation data used for the acquisition in a non-transitory storage medium; and processing the stored data to reconstruct a first extended field view (EFOV) image; cropping the first EFOV image to generate the prescribed FOV image without aliasing or wrap artifacts; and displaying the prescribed (FOV) image; and reusing the stored data to re-reconstruct a second extended (EFOV) image; and displaying the second extended field of view (EFOV) image.

2. The method of reconstructing an image of a subject in a MRI IT system of claim 1 wherein: the non-transitory storage medium is a PACS (Picture Archiving and Communications System) and/or a technician workstation.

3. The method of reconstructing an image of a subject in a MRI IT system of claim 2 wherein: the PACS and/or technician workstation further stores executable instructions for the re-reconstruction of the second extended (EFOV) image.

4. The method of reconstructing an image of a subject in a MRI IT system of claim 1 wherein: the display of the of the prescribed (FOV) image contains an indication that the second (EFOV) image is available.

5. The method of reconstructing an image of a subject in a MRI IT system of claim 1 wherein: the display of the of the prescribed (FOV) image contains in indication that the second (EFOV) image may contain aliasing and wrap artifacts.

6. The method of reconstructing an image of a subject in a MRI IT system of claim 1 wherein: the re-reconstruction of the second extended (EFOV) image is performed in the phase encode (PE) direction.

7. The method of reconstructing an image of a subject in a MRI IT system of claim 1 wherein: the re-reconstruction of the second extended (EFOV) image is performed in the slice select (SS) direction.

8. A device for reconstructing an image of a subject in a MRI IT system by repurposing image data comprising: a non-transitory storage medium for storing acquired k-space data including oversampling k-space data for a plurality of prescribed field of view (FOV) images that are adjacent or overlapping of the subject and have the same angulation; and a processor for processing the stored data to reconstruct at least one of the prescribed field of view (FOV) images and an extended field of view (EFOV) image of the prescribed FOV image without any aliasing or wrap artifacts by repurposing k-space oversampling data from said adjacent or overlapping prescribed (FOV) images; and a display for displaying the prescribed (FOV) image and the extended field of view (EFOV) image.

9. The device for reconstructing an image of claim 8 wherein: the non-transitory storage medium is in a PACS and/or a technician workstation.

10. The device for reconstructing an image of claim 9 wherein: the PACS and/or a technician workstation further stores executable instructions to perform the reconstruction of the extended (EFOV) image.

11. The device for reconstructing an image of claim 8 wherein: the display of the prescribed (FOV) image contains an indication that the extended field of view (EFOV) image is available.

12. The device for reconstructing an image of claim 8 wherein: a user interface is provided to control the processor to reconstruct the extended field view (FOV) image.

13. The device for reconstructing an image of claim 8 wherein: the plurality of prescribed field of view (FOV) images correspond to adjacent body parts of the subject.

14. The device for reconstructing an image of claim 12 wherein: the plurality of prescribed field of view (FOV) images correspond to successive adjacent stations of a multi-station examination of the subject.

15. The device for reconstructing an image of claim 12 wherein: the adjacent body parts correspond to the spine of the subject.

16. The device for reconstructing an image of claim 12 wherein: the prescribed field of view (FOV) images include; thoracic, cervical and lumbar images of the subject.

17. A method of repurposing image data in a MRI IT examination of a subject comprising: acquiring k-space data including oversampling k-space data for a plurality of prescribed field of view (FOV) images of the subject that are adjacent or overlapping and have the same angulation; and storing the acquired data in a non-transitory storage medium; and
    processing the stored data to reconstruct at least one of the prescribed field of view (FOV) images and an extended field of view (EFOV) image of the prescribed FOV image without any aliasing or wrap artifacts by repurposing k-space oversampling data from said adjacent or overlapping prescribed (FOV) images; displaying the prescribed (FOV) image and the extended field of view (EFOV) image.

18. The method of repurposing image data of claim 17 wherein; the non-transitory storage medium is a PACS (Picture Archiving and Communications System) and/or a technician workstation.

19. he method of repurposing image data of claim 18 wherein; the PACS (Picture Archiving and Communications System) and/or the technician workstation, further stores tagged metadata.

20. The method of repurposing image data of claim 19 wherein; the metadata is stored as data acquisition parameters for the MRI IT examination of the subject.

21. The method of repurposing image data of claim 19 wherein; the oversampling data is phase or frequency oversampling data.

* * * * *